US008865927B2

(12) United States Patent
Katsoulis et al.

(10) Patent No.: US 8,865,927 B2
(45) Date of Patent: Oct. 21, 2014

(54) METHOD FOR PREPARING A DIORGANODIHALOSILANE

(71) Applicant: Dow Corning Corporation, Midland, MI (US)

(72) Inventors: Dimitris Katsoulis, Midland, MI (US); Robert Larsen, Midland, MI (US); Matthew McLaughlin, Midland, MI (US); Wendy Sparschu, Bay City, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/343,407

(22) PCT Filed: Oct. 10, 2012

(86) PCT No.: PCT/US2012/059487
§ 371 (c)(1),
(2), (4) Date: Mar. 7, 2014

(87) PCT Pub. No.: WO2013/074219
PCT Pub. Date: May 23, 2013

(65) Prior Publication Data
US 2014/0243494 A1    Aug. 28, 2014

Related U.S. Application Data

(60) Provisional application No. 61/561,077, filed on Nov. 17, 2011.

(51) Int. Cl.
*C07F 7/12* (2006.01)
*C07F 7/14* (2006.01)
*C08G 77/04* (2006.01)

(52) U.S. Cl.
CPC .. *C07F 7/14* (2013.01); *C08G 77/04* (2013.01)
USPC ........... 556/478; 556/465; 556/466; 556/472; 556/473; 528/10

(58) Field of Classification Search
None
See application file for complete search history.

(56) References Cited

U.S. PATENT DOCUMENTS

| 4,888,435 | A | 12/1989 | Chadwick et al. |
| 4,956,326 | A | 9/1990 | Yoneda et al. |
| 5,427,952 | A | 6/1995 | Daugherty et al. |
| 5,716,590 | A | 2/1998 | Roewer et al. |
| 6,887,448 | B2 | 5/2005 | Block et al. |
| 8,674,129 | B2 * | 3/2014 | Dash et al. ............... 556/466 |
| 8,697,900 | B2 * | 4/2014 | Anderson et al. ......... 556/466 |
| 8,765,090 | B2 * | 7/2014 | Katsoulis et al. ......... 423/342 |
| 8,772,525 | B2 * | 7/2014 | Katsoulis et al. ......... 556/478 |

FOREIGN PATENT DOCUMENTS

| CA | 2829701 A1 | 9/2012 |
| DE | 4041644 A1 | 6/1992 |
| WO | 2013074425 A1 | 5/2013 |
| WO | 2014028417 A2 | 2/2014 |
| WO | 2014062255 A1 | 4/2014 |

OTHER PUBLICATIONS

Mulla, et. al., "Reaction of Magnesium Silicide & Silicon Tetrachloride/Trichlorosilane in Presence of Hydrogen", Indian Journal of Chemistry, Sep. 1988, pp. 756-758, vol. 27A.
Walter, et. al., "Mechanism of the silicide-catalysed hydrodehalogenation of silicon tetrachloride to trichlorosilane", J. Chem. Soc., Faraday Trans., 1996, pp. 4605-4608, 92(22), Freiberg, Germany.

* cited by examiner

*Primary Examiner* — Marc Zimmer
(74) *Attorney, Agent, or Firm* — Catherine U. Brown

(57) ABSTRACT

A method of preparing a diorganodihalosilane, the method comprising the following separate and consecutive steps: (a) treating a metal catalyst comprising a metal selected from the groups consisting of i) gold, ii) gold and copper, iii) gold, copper and magnesium, iv) copper, rhodium and gold, v) copper, rhodium, and rhenium, vi) rhenium and palladium, vii) copper, and viii) copper and magnesium with a mixture comprising hydrogen gas and an organotrihalosilane at a temperature from 500 to 1400° C. to form a silicon-containing metal intermediate; and (b) reacting the silicon-containing metal intermediate with an organohalide according to the formula RX, wherein R is $C_1$-$C_{10}$ hydrocarbyl and X is halo, at a temperature from 100 to 600° C. to form a diorganodihalosilane and a depleted silicon-containing metal intermediate.

19 Claims, No Drawings

METHOD FOR PREPARING A DIORGANODIHALOSILANE

CROSS REFERENCE TO RELATED APPLICATIONS

This application is a U.S. national stage filing under 35 U.S.C. §371 of PCT Application No. PCT/US12/059487 filed on Oct. 10, 2012, currently pending, which claims the benefit of U.S. Provisional Patent Application No. 61/561,077 filed Nov. 17, 2011 under 35 U.S.C. §119 (e). PCT Application No. PCT/US12/059487 and U.S. Provisional Patent Application No. 61/561,077 are hereby incorporated by reference.

Diorganodihalosilanes are hydrolyzed to produce a wide range of polyorganosiloxanes, which are sold into many different industries. Typically, diorganodihalosilanes are produced commercially by the Mueller-Rochow Direct Process, which comprises passing an organohalide, such as methyl chloride, over zero-valent silicon in the presence of a metal catalyst and various promoters to produce a mixture of organohalosilanes. Of the organhalosilanes produced in the Direct Process, dimethyldichlorosilane is the most valuable.

A typical commercial process to make zero-valent silicon comprises the carbothermic reduction of $SiO_2$ in an electric arc furnace at extremely high temperatures. Generation of these extreme temperatures requires significant amounts of energy, which adds significant cost to the process of producing zero-valent silicon. Consequently, the use of zero-valent silicon also adds significant costs to the production of diorganodihalosilanes.

In addition to the Direct Process, diorganodihalosilanes have been produced by the alkylation of silicon tetrachloride and various methylchlorosilanes by passing the vapors of these chlorosilanes together with an alkyl halide over finely divided aluminum or zinc at elevated temperatures. However, this process results in the production of a large amount of aluminum chloride or zinc chloride, which is costly to dispose of on a commercial scale.

Therefore, there is a need for a more economical method of producing diorganodihalosilanes that reduces or avoids the need for zero-valent silicon produced by reducing $SiO_2$ at extremely high temperatures and that does not require the costly disposal of byproducts.

BRIEF SUMMARY OF THE INVENTION

The present invention is directed to a method of preparing a diorganodihalosilane comprising the following separate and consecutive steps: (a) treating a metal catalyst comprising a metal selected from the group consisting of i) gold, ii) gold and copper, iii) gold, copper and magnesium, iv) copper, rhodium and gold, v) copper, rhodium, and rhenium, vi) rhenium and palladium, vii) copper, and viii) copper and magnesium with a mixture comprising hydrogen gas and an organotrihalosilane at a temperature from 500 to 1400° C. to form a silicon-containing metal intermediate; and (b) reacting the silicon-containing metal intermediate with an organohalide according to the formula RX, wherein R is $C_1$-$C_{10}$ hydrocarbyl and X is halo, at a temperature from 100 to 600° C. to form a diorganodihalosilane and a depleted silicon-containing metal intermediate.

The method of the present invention produces a diorganodihalosilane from an organotrihalosilane. Since an organotrihalosilane may be a lower-value product or byproduct of industrial processes, the method of the invention may be more economical than other processes for producing diorganodihalosilanes. Furthermore, the method does not produce large amounts of metal halide byproducts requiring costly disposal. Finally, the method produces the more valuable diorganodihalosilane with good selectivity compared to the other organosilanes produced.

The diorganodihalosilane produced by the method of the invention can be hydrolyzed in known processes to produce polyorganosiloxanes. The polyorganosiloxanes thus produced find use in many industries and applications.

DETAILED DESCRIPTION OF THE INVENTION

A method of preparing a diorganodihalosilane, the method comprising the following separate and consecutive steps:

(a) treating a metal catalyst comprising a metal selected from the group consisting of i) gold, ii) gold and copper, iii) gold, copper and magnesium, iv) copper, rhodium and gold, v) copper, rhodium, and rhenium, vi) rhenium and palladium, vii) copper, and viii) copper and magnesium with a mixture comprising hydrogen gas and an organotrihalosilane at a temperature from 500 to 1400° C. to form a silicon-containing metal intermediate; and (b) reacting the silicon-containing metal intermediate with an organohalide according to the formula RX, wherein R is $C_1$-$C_{10}$ hydrocarbyl and X is halo, at a temperature from 100 to 600° C. to form a diorganodihalosilane and a depleted silicon-containing metal intermediate.

In step (a), a metal catalyst comprising a metal selected from the group consisting of i) gold, ii) gold and copper, iii) gold, copper and magnesium, iv) copper, rhodium and gold, v) copper, rhodium, and rhenium, vi) rhenium and palladium, vii) copper, and viii) copper and magnesium is treated with a mixture comprising hydrogen gas and an organotrihalosilane at a temperature from 500 to 1400° C. to form a silicon-containing metal intermediate.

The metal catalyst can be a supported or unsupported metal catalyst. Examples of supports include, but are not limited to, oxides of aluminum, titanium, zirconium, and silicon; activated carbon; carbon nanotubes; fullerenes; and other allotropic forms of carbon. In one embodiment, the support is activated carbon.

When the metal catalyst comprises a support, the catalyst typically comprises from 0.1 to less than 100% (w/w), alternatively from 0.1 to 50% (w/w), alternatively from 0.1 to 35% (w/w), of a metal or a mixture of metals, based on the combined weight of the support and copper or the mixture.

The metal catalyst can have a variety of physical forms including, but not limited to, lumps, granules, flakes, and powder.

Examples of the unsupported metal catalysts include, but are not limited to, metallic gold; mixtures of metallic gold and copper; mixtures of metallic gold, metallic copper and magnesium chloride; mixtures of metallic copper, metallic rhodium and metallic gold; mixtures of metallic copper, metallic rhodium, and metallic rhenium; mixtures of metallic rhenium and metallic palladium; metallic copper; and mixtures of metallic copper and magnesium. As used herein, "metallic" means that the metal has an oxidation number of zero.

Examples of the supported metal catalysts include the unsupported metal catalysts described above on an activated carbon support, where the supported metal catalyst comprises from 0.1 to 35% (w/w) of at least one metal, based on the weight of the support and the metal.

The unsupported and supported metal catalysts can be made by processes known in the art. For example, to make the unsupported metal catalyst, metallic copper and gold may be mixed. In addition, metal salts, including, but not limited to, halide, acetate, nitrate, and carboxylate salts, may be mixed in desired proportions and then subjected to known reduction processes. One such reduction process is described below for making the supported metal catalyst. This process may leave some salts, such as magnesium chloride, unreduced, while reducing others.

The supported metal catalyst may be prepared by, for example, making a mixture of a metal salt, such as gold chloride, in a solvent, such as water or acid, applying the mixture to a support, and reducing the gold salt on the surface of the support. For example, Au(I)Cl can be dissolved in water or hydrochloric acid and mixed with activated carbon. Excess Au(I)Cl solution can then be removed, and the activated carbon—Au(I)Cl mixture dried. The Au(I)Cl can then be reduced on the activated carbon with hydrogen at 500° C. to give the supported metal catalyst. One skilled in the art would understand that the order of addition, reduction and multistep addition of salts and subsequent reduction can also be carried out to prepare the supported catalyst. Some of these catalysts are also available commercially.

The organotrihalosilane is according to the formula $RSiX_3$ (I), wherein R is $C_1$-$C_{10}$ hydrocarbyl, and X is halo, for example, chloro, bromo, fluoro, or iodo.

The hydrocarbyl groups represented by R typically have from 1 to 10 carbon atoms, alternatively from 1 to 6 carbon atoms, alternatively from 1 to 4 carbon atoms, alternatively 1 carbon atom. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl; cycloalkyl, such as cyclopentyl, coclohexyl, and methylcyclohexyl; aryl, such as phenyl and napthyl; alkaryl, such as tolyl and xylyl; aralkyl, such as benzyl and phenethyl; alkenyl, such as vinyl, allyl, and propenyl; aralkenyl, such as styryl and cinnamyl; and alkynyl, such as ethynyl and proynyl.

Examples of the organotrihalosilane include methyltrichlorosilane ($CH_3SiCl_3$), methyltribromosilane, methyltrifluorosilane, methyltriiodosilane, ethyltrichlorosilane, ethyltribromosilane, ethyltrifluorosilane, ethyltriiodosilane, propyltrichlorosilane, propyltribromosilane, propyltrifluorosilane, propyltriiodosilane, butyltrichlorosilane, butyltribromosilane, butyltrifluorosilane, butyltriiodosilane, phenyltrichlorosilane, phenyltribromosilane, phenyltrifluorosilane, phenyltriiodosilane, benzyltrichlorosilane, benzyltribromosilane, benzyltrifluorosilane, and benzyltriiodosilane. In one embodiment, the organotrihalosilane is methyltrichlorosilane.

Methods of making organotrihalosilanes are known in the art. Many of these compounds are available commercially.

The reactor for step (a) can be any reactor suitable for the combining of gases and solids. For example, the reactor configuration can be a packed bed, stirred bed, vibrating bed, moving bed, re-circulating beds, or a fluidized bed. When using re-circulating beds, the silicon-containing metal catalyst can be circulated from a bed for conducting step (a) to a bed for conducting step (b). To facilitate reaction, the reactor should have means to control the temperature of the reaction zone.

The temperature at which the metal catalyst is treated with the hydrogen and the organotrihalosilane is typically from 500 to 1400° C.; alternatively from 600 to 1200° C.; alternatively from 650 to 1100° C.

The pressure at which the metal catalyst is treated with the hydrogen and the organotrihalosilane can be sub-atmospheric, atmospheric, or super-atmospheric. For example, the pressure is typically from 100 to 2000 kilopascals gauge (kPag); alternatively from 100 to 1000 kPag; alternatively from 100 to 800 kPag, at a temperature from 500 to 1400° C.

The mole ratio of hydrogen to organotrihalosilane in step (a) is from 10,000:1 to 0.01:1, alternatively from 100:1 to 1:1, alternatively from 20:1 to 2:1, alternatively from 20:1 to 5:1.

The residence time for the hydrogen and organotrihalosilane in step (a) is sufficient for the hydrogen and organotrihalosilane to contact the metal catalyst and form the silicon-containing metal intermediate. For example, a sufficient residence time for the hydrogen and organotrihalosilane is typically at least 0.01 seconds (s); alternatively at least 0.1 s; alternatively from 0.1 s to 10 min; alternatively from 0.1 s to 1 min; alternatively from 0.5 s to 10 s. As used herein, "residence time" means the time for one reactor volume of reactant gases (i.e., hydrogen and organotrihalosilane or organohalide) to pass through a reactor charged with metal catalyst. The desired residence time may be achieved by adjusting the flow rate of the hydrogen and organotrihalosilane.

The hydrogen and organotrihalosilane are typically fed to the reactor simultaneously; however, other methods of combining, such as by separate pulses, are also envisioned.

The metal catalyst is in a sufficient amount. As used herein, a "sufficient amount" of metal catalyst is enough catalyst to form the silicon-containing metal intermediate, described below, when the metal catalyst is treated with hydrogen and organotrihalosilane. For example, a sufficient amount of catalyst is at least 0.01 mg catalyst/$cm^3$ of reactor volume; alternatively at least 0.5 mg catalyst/$cm^3$ of reactor volume; alternatively from 1 to 10,000 mg catalyst/$cm^3$ of reactor volume.

There is no upper limit on the time for which step (a) is conducted. For example, step (a) is usually conducted for at least 0.1 seconds, alternatively from 1 second to 5 hours, alternatively from 1 minute to 1 hour.

In step (b) of the method, the silicon-containing metal intermediate is reacted with an organohalide according to the formula RX, wherein R is $C_1$-$C_{10}$ hydrocarbyl and X is halo, at a temperature of from 100 to 600° C. to form at least one diorganodihalosilane and a depleted silicon-containing metal intermediate.

The silicon-containing metal intermediate comprises at least 0.1% (w/w), alternatively from 0.1 to 90% (w/w), alternatively 1 to 20% (w/w), alternatively from 1 to 5% (w/w), based on the total weight of silicon-containing metal intermediate including any support, of silicon. The percentage of silicon in the silicon-containing metal intermediate can be determined using standard analytical tests. For example, the percentage of silicon may be determined using inductively coupled plasma atomic emission spectroscopy (ICP-AES) and ICP mass spectrometry (ICP-MS).

The organohalide has the formula RX, wherein R is $C_1$-$C_{10}$ alkyl or $C_4$-$C_{10}$ cycloalkyl, and X is as defined above for the organotrihalosilane and may be the same or different as the organotrihalosilane.

The alkyl groups represented by R typically have from 1 to 10 carbon atoms, alternatively from 1 to 6 carbon atoms, alternatively from 1 to 4 carbon atoms. The cycloalkyl groups represented by R typically have from 4 to 10 carbon atoms; alternatively 6 to 8 carbon atoms. Alkyl groups containing at least three carbon atoms can have a branched or unbranched structure. Examples of alkyl groups include, but are not limited to, methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2- dimethylpropyl, 2,2-dimethylpropyl, hexyl, heptyl, octyl, nonyl, and decyl. Examples of cycloalkyl groups include, but are not limited to, cyclobutyl, cyclopentyl, cyclohexyl, and methylcyclohexyl.

Examples of the organohalide include, but are not limited to, methyl chloride, methyl bromide, methyl iodide, ethyl chloride, ethyl bromide, ethyl iodide, cyclobutyl chloride, cyclobutyl bromide, cyclohexyl chloride, and cyclohexyl bromide.

The reactors suitable for use in step (b) are as described for step (a). The same reactor may be used for step (a) as used in step (b); however, separate reactors may also be used.

The organohalide is typically reacted with the silicon-containing metal intermediate by feeding the organohalide into a reactor containing the silicon-containing metal intermediate produced in step (a).

The residence time of the organohalide is sufficient for the organohalide to react with the silicon-containing metal intermediate to form a diorganodihalosilane. For example, a sufficient residence time of the organohalide is typically at least 0.01 s, alternatively at least 0.1 s, alternatively from 0.5 s to 10 min, alternatively from 1 s to 1 min, alternatively from 1 to 10 s. The desired residence time can be achieved by adjusting the flow rate of the organohalide.

The temperature at which organohalide is reacted with the silicon-containing metal intermediate is typically from 100 to 600° C.; alternatively from 200 to 500° C.; alternatively from 250 to 375° C.

Step (b) is typically conducted until the silicon in the silicon-containing metal intermediate falls below predetermined limits. For example, step (b) is typically conducted until the silicon in the silicon-containing metal intermediate is below 90% (w/w), alternatively from 1 to 90% (w/w), alternatively from 1 to 40% (w/w), of its initial weight percent, based on the total weight of catalyst including any support. As used herein, the "initial weight percent of silicon in the silicon-containing metal intermediate" means the weight percent of silicon in the silicon-containing metal intermediate before the silicon-containing metal intermediate is reacted with the organohalide in step (b). The amount of silicon in the silicon-containing metal intermediate can be monitored by correlating diorganodihalosilane production with the weight percent of silicon in the silicon-containing metal intermediate and then monitoring diorganodihalosilane production or may be determined as described above for the silicon-containing metal intermediate.

The pressure at which the organohalide is reacted with the silicon-containing metal intermediate in step (b) can be sub-atmospheric, atmospheric, or super-atmospheric. For example, the pressure is typically from 100 to 2000 kilopascals gauge (kPag); alternatively from 100 to 1000 kPag; alternatively from 100 to 800 kPag.

The silicon-containing metal intermediate is in a sufficient amount. As used herein, a "sufficient amount" of silicon-containing metal intermediate is enough catalyst to form the diorganodihalosilane, described below, when reacted with the organohalide. For example, a sufficient amount of silicon-containing metal intermediate is at least 0.01 mg catalyst/cm$^3$ of reactor volume; alternatively at least 0.5 mg catalyst/cm$^3$ of reactor volume; alternatively from 1 to 10000 mg catalyst/cm$^3$ of reactor volume.

Step (a) and step (b) of the method are conducted separately and consecutively. As used herein, "separately" means that the step (a) and step (b) do not overlap or coincide. As used herein, "consecutively" means that step (b) is performed after step (a) in the method; however, additional steps may be performed between step (a) and (b), such as described below.

The method of the invention may also comprise purging prior to the contacting of the silicon-containing metal intermediate with the organohalide in step (b) and prior to the contacting of the reformed silicon-containing metal intermediate with the organohalide in step (d). As used herein, "purging" means to introduce a gas stream to the reactor containing the silicon-containing metal intermediate to remove unwanted materials. Unwanted materials are, for example, $H_2$, $O_2$, and $H_2O$. Purging may be accomplished with an inert gas, such as argon, or with a reactive gas, such as silicon tetrachloride, which reacts with moisture thereby removing it.

In one embodiment of the invention, the silicon-containing metal intermediate and the organohalide reacted in step (b) are reacted in the absence of hydrogen, organotrihalosilane, or both hydrogen and organotrihalosilane.

In one embodiment, the method further comprises (c) contacting the silicon-containing metal intermediate reacted with the organohalide in step (b) with the mixture comprising hydrogen gas and a organotrihalosilane at a temperature of from 500 to 1400° C. to reform the silicon-containing metal intermediate comprising at least 0.1% (w/w) silicon; and (d) contacting the reformed silicon-containing metal intermediate with the organohalide at a temperature of from 100 to 600° C. to form at least one diorganodihalosilane.

In another embodiment, the method of the invention further comprises repeating steps (c) and (d) at least 1 time, alternatively from 1 to $10^5$ times, alternatively from 1 to 1000 times, alternatively from 1 to 100 times, alternatively from 1 to 10 times.

If the organohalide or organotrihalosilane are liquids at or below standard temperature and pressure, the method may further comprise pre-heating and gasifying the organohalide or organotrihalosilane by known methods prior to contacting the organotrihalosilane with the metal catalyst in step (a) and (c) or contacting the organohalide with the silicon-containing metal intermediates in step (b) and (d). Alternatively, the process may further comprise bubbling the hydrogen through liquid organotrihalosilane to vaporize the organotrihalosilane prior to contacting with the metal catalysts in step (a) and the silicon-containing metal intermediate in (c).

The process may further comprise recovering the diorganodihalosilane produced. The diorganodihalosilane may be recovered by, for example, removing gaseous diorganodihalosilane from the reactor followed by isolation by distillation.

The diorganodihalosilane produced by the process described and exemplified above has the formula $R_2SiX_2$, wherein R and X are as defined and exemplified above for the organohalide.

Examples of diorganodihalosilanes prepared according to the present process include, but are not limited to, dimethyldichlorosilane (i.e., $(CH_3)_2SiCl_2$), dimethyldibromosilane, dimethyldiiodosilane, dimethyldifluorosilane, diethyldichlorosilane, diethyldibromosilane, diethyldiiodosilane, dicyclohexyldichlorosilane, and dicyclohexyldibromosilane.

The process may also produce other organohalosilanes, such as those having the formula $R_aHSiX_{3-a}$, $RSiX_3$, and $R_3SiX$, where R and X are as defined above and a is 1 or 2. The process may also produce hydrohalosilanes, such as those having the formula $HSiX_3$, where X is as defined above.

Step (b) and (d) produce a depleted silicon-containing metal catalyst. The depleted silicon-containing metal catalyst has had the silicon deposited in steps (a) and (c) reacted with the organohalide to form the diorganodihalosilane. Therefore, the depleted silicon-containing metal catalyst has been depleted of silicon compared to the silicon-containing metal catalyst prepared in steps (a) and (c).

The method of the present invention produces diorganodihalosilanes from organotrihalosilane. Since organotrihalosilane is a byproduct of other industrial processes and may be produced using less energy than required to produce zero-valent silicon, the method of the invention may be more economical than methods of producing diorganodihalosilanes using zero-valent silicon. Furthermore, the method does not produce large amounts of metal halide byproducts requiring costly disposal. Still further, the method produces the more valuable diorganodihalosilanes with good selectivity compared to other organosilanes. Finally, the metal catalyst may be reformed and reused in the method, and the reforming and reuse provides increasing diorganodihalosilane production and selectivity.

The process of the present invention produces diorganodihalosilanes that can be hydrolyzed in known processes for producing polyorganosiloxanes. The polyorganosiloxanes thus produced find use in many industries and applications.

EXAMPLES

The following examples are presented to better illustrate the method of the present invention, but are not to be considered as limiting the invention, which is delineated in the appended claims. Unless otherwise noted, all parts and percentages reported in the examples are by weight. The following table describes the abbreviations and terms used in the examples:

TABLE 1

List of abbreviations and terms used in the examples.

| Abbreviation | Word |
| --- | --- |
| g | gram |
| mg | milligram |
| Me | methyl |
| wt | weight |
| % | percent |
| mol | mole |
| hr | hour |
| °C. | degrees Celsius |
| NA | Not Applicable |
| mL | milliliters |
| cm | centimeter |
| sccm | standard cubic centimeters per minute |
| TCD | thermal conductivity detector |
| Sel. | selectivity |
| $Me_2SiCl_2$ Selectivity | weight of dimethyldichlorosilane divided by the sum of the weights all other volatile Si containing products |
| $Me_2SiCl_2$ wt. % | weight percent of $Me_2SiCl_2$ leaving the reactor based upon the total mass leaving the reactor |
| GC | gas chromatograph |
| Et | Ethyl |
| Pr | Propyl |
| n-Pr | n-Propyl |

Example 1

A 18 wt % Cu/0.6 wt % Au/0.2 wt % $MgCl_2$ catalyst was prepared as follows: 0.0194 g $AuCl_3$ (99+%, Sigma Aldrich) and 0.0363 g $MgCl_2*6H_2O$ (99+%, Sigma Aldrich) were added to 0.1 mL HCl and 2.1 mL de-ionized water and allowed to dissolve. This was added to 0.8317 g $CaCl_2*2H_2O$ (99+%, Alfa Aesar) and the $CuCl_2$ was allowed to dissolve. The solution was then added to 1.1418 g C. Any excess solution was drained off and the mixture was dried at 170° C. for 24 hours. 0.69 g of this catalyst was loaded into a quartz tube and placed in a custom built stainless steel flow tube reactor inside of a tube furnace (Lindberg/Blue Minimite tube furnace). The catalyst was reduced for 2 hours at 600° C. under 100 sccm of $H_2$ after which the temperature was brought to 650° C. At this point, n-$PrSiCl_3$ was introduced over the catalyst by first bubbling the 100 sccm of $H_2$ gas stream through liquid n-$PrSiCl_3$ contained in a vapor bubbler at room temperature (giving approximately 2.0 sccm n-$PrSiCl_3$ vapor flow rate) to form a silicon-containing metal intermediates. Next, the silicon-containing metal intermediate was cooled under 100 sccm $H_2$ to 300° C. after which the reactor was purged with Ar for 30 minutes. After 30 minutes 1 sccm MeCl was flowed over the silicon-containing metal intermediate at 300° C. for 66 minutes, and ethylated chlorosilanes eluted from the reactor. The chlorosilanes that eluted were characterized by an Agilent GC-MS with fast LTM column modules and SPB-Octyl columns (30 m long× 250 um i.d., Supelco) and the injection was sampled directly from the reactor exit via a 6-way valve with 100 uL sample loop (Valco). Approximately 25 mg of $Me_2SiCl_2$ was produced after 66 minutes along with lesser amounts of $MeSiCl_3$, $MeHSiCl_2$, $Me_2HSiCl$, $Me_3SiCl$, n-$PrSiCl_3$, n-$PrMeSiCl_2$, n-$PrHSiCl_2$, allyl-$SiCl_3$, $EtSiCl_3$, $EtMeSiCl_2$, $Me_4Si$, and $ClMe_2SiOCH_2CH_2OSiMe_2Cl$ Example 2

A metal catalyst (0.4856 g) comprising an activated carbon supported mixture of 22.3% (w/w) Cu, 0.7% (w/w) Au, and 0.2% (w/w) Mg (prepared using the procedure used to make the catalyst in example 1) was treated with $H_2$ and $MeSiCl_3$ at a mole ratio of $H_2$ to $MeSiCl_3$ of 17:1 for 30 min by bubbling $H_2$ (100 sccm) through a stainless steel bubbler containing liquid $MeSiCl_3$ at about 1.5° C. and into a flow reactor containing the metal catalyst at 750° C. to form a silicon-containing metal intermediate. After 30 minutes, the $MeSiCl_3$ flow was ceased, and the hydrogen flow was maintained for about 1 hr. while cooling the reactor to 300° C.

The reactor containing the silicon-containing metal intermediate was then purged with a 50 sccm argon flow for 15 min. After the purging, MeCl was fed through the reactor at a flow rate of 5 sccm. The reaction effluent was periodically analyzed by GC to determine the $Me_2SiCl_2$ selectivity. After the silane production rate declined, the MeCl feed was ceased, and the catalyst was treated again with $H_2$ and $MeSiCl_3$ for 30 min at 750° C. to reform the silicon-containing metal intermediate. The reformed silicon-containing metal intermediate was then purged with argon and reacted again with MeCl as described above.

This cycle of treating the metal catalyst with $H_2$ and $MeSiCl_3$ to form the silicon-containing catalyst and exposing the silicon-containing metal intermediate formed to MeCl was performed a total of five times with the same metal catalyst. In some cycles, the temperature of reaction, the pressure of the reaction, or the bubbler temperature were changed. Each cycle's conditions and the selectivity results are shown in Table 2.

TABLE 2

| Cycle # | Step 1 | Step 2 | Time (min) | Selectivity (mol % Si products) $Me_2SiCl_2$ | Wt. % $Me_2SiCl_2$ in effluent |
| --- | --- | --- | --- | --- | --- |
| 1 | $H_2$: 100 sccm $MeSiCl_3$: 5.8 | MeCl: 5 sccm | 3 24 | 10.5 58.2 | 0.04 1.6 |

TABLE 2-continued

| Cycle # | Step 1 | Step 2 | Time (min) | Selectivity (mol % Si products) Me$_2$SiCl$_2$ | Wt. % Me$_2$SiCl$_2$ in effluent |
|---|---|---|---|---|---|
|  | sccm<br>Temp: 750° C.<br>P: 146 kPa | Temp: 300° C.<br>P: 109 kPa | 45<br>67<br>89<br>117 | 15.5<br>1.5<br>0<br>0 | 0.2<br>0.02<br>0<br>0 |
| 2 | H$_2$: 100 sccm<br>MeSiCl$_3$: 6.9 sccm<br>Temp: 750° C.<br>P: 118 kPa | MeCl: 5 sccm<br>Temp: 300° C.<br>P: 105 kPa | 3<br>23<br>48<br>77<br>99<br>125 | 0<br>40.8<br>0<br>0<br>0<br>0 | 0<br>0.3<br>0<br>0<br>0<br>0 |
| 3 | H$_2$: 100 sccm<br>MeSiCl$_3$: 6.7 sccm<br>Temp: 750° C.<br>P: 121 kPa | MeCl: 5 sccm<br>Temp: 300° C.<br>P: 107 kPa | 4<br>24<br>48<br>68<br>95 | 0<br>30.5<br>0<br>0<br>0 | 0<br>0.1<br>0<br>0<br>0 |
| 4 | H$_2$: 100 sccm<br>MeSiCl$_3$: 7.4 sccm<br>Temp: 750° C.<br>P: 121 kPa | MeCl: 5 sccm<br>Temp: 400° C.<br>P: 106 kPa | 20<br>40<br>62 | 0.6<br>0<br>0 | 0.1<br>0<br>0 |
| 5 | H$_2$: 100 sccm<br>MeSiCl$_3$: 2.7 sccm<br>Temp: 750° C.<br>P: 798 kPa | MeCl: 5 sccm<br>Temp: 300° C.<br>P: 108 kPa | 20<br>46<br>66 | 2.5<br>0<br>0 | 0.1<br>0<br>0 |

Example 3

A metal catalyst comprising 20.9% Cu and 0.6% Au on activated carbon was prepared and treated as described in example 2. One cycle of treating the metal catalyst to form the silicon-containing metal intermediate was performed; the stainless steel bubbler was at 24° C. to give a mole ratio of H$_2$ to MeSiCl$_3$ of 5:1 in forming the silicon-containing metal intermediate. After forming the silicon-containing metal intermediate, it was reacted with MeCl in example 2 at 300° C. All of the parameters and results are listed in Table 3.

TABLE 3

| Cycle # | Step 1 | Step 2 | Time (min) | Selectivity (mol % Si products) Me$_2$SiCl$_2$ | Wt. % Me$_2$SiCl$_2$ in effluent |
|---|---|---|---|---|---|
| 1 | H$_2$: 100 sccm<br>MeSiCl$_3$: 19.7 sccm<br>Temp: 650° C.<br>P: 125 kPa | MeCl: 5 sccm<br>Temp: 300° C.<br>P: 106 kPa | 9<br>30<br>59<br>78<br>98 | 24.6<br>1.4<br>0<br>0<br>0 | 0.05<br>0.02<br>0<br>0<br>0 |

Example 4

A metal catalyst comprising 14.9% Au on activated carbon was prepared and treated as described in example 2. Three cycles were conducted, where a cycle comprised generating the silicon-containing metal intermediate, reacting the silicon-containing metal intermediate with MeCl, then regenerating the silicon-containing metal intermediate from the MeCl-reacted, silicon-containing catalyst. During the cycles, the stainless steel bubbler was kept at 0-10° C. while MeSiCl$_3$ was passed over the metal catalyst to form the silicon-containing metal intermediate. The silicon-containing metal intermediate was reacted with MeCl as in example 2 at 300° C. All of the parameters and results are listed in Table 4.

TABLE 4

| Cycle # | Step 1 | Step 2 | Time (min) | Selectivity (mol % Si products) Me$_2$SiCl$_2$ | Wt. % Me$_2$SiCl$_2$ in effluent |
|---|---|---|---|---|---|
| 1 | H$_2$: 100 sccm<br>MeSiCl$_3$: 6.8 sccm<br>Temp: 650° C.<br>P: 127 kPa | MeCl: 5 sccm<br>Temp: 300° C.<br>P: 114 kPa | 4<br>24<br>45<br>65 | 0<br>3.7<br>0<br>0 | 0<br>0.01<br>0<br>0 |
| 2 | H$_2$: 100 sccm<br>MeSiCl$_3$: 11.7 sccm<br>Temp: 650° C.<br>P: 132 kPa | MeCl: 5 sccm<br>Temp: 300° C.<br>P: 116 kPa | 21<br>41<br>62 | 13.4<br>0<br>0 | 0.01<br>0<br>0 |
| 3 | H$_2$: 100 sccm<br>MeSiCl$_3$: 9.9 sccm<br>Temp: 750° C.<br>P: 134 kPa | MeCl: 5 sccm<br>Temp: 300° C.<br>P: 117 kPa | 23<br>47<br>70<br>93 | 0<br>29.8<br>31.5<br>34.8 | 0<br>0.01<br>0.01<br>0.01 |

Example 5

A metal catalyst comprising 4.9% Cu, 2.5% Rh, and 0.3% Au on activated carbon was prepared and treated as described in example 2. Two cycles, where a cycle is as described in example 4, of the reaction were performed; the stainless steel bubbler was kept at room temperature while MeSiCl$_3$ was passed over the metal catalyst to form the silicon-containing metal intermediate. The silicon-containing metal intermediate was reacted with MeCl as described in example 2 at 300° C. All of the parameters and results are listed in Table 5.

TABLE 5

| Cycle # | Step 1 | Step 2 | Time (min) | Selectivity (mol % Si products) Me$_2$SiCl$_2$ | Wt. % Me$_2$SiCl$_2$ in effluent |
|---|---|---|---|---|---|
| 1 | H$_2$: 100 sccm<br>MeSiCl$_3$: 4.9 sccm<br>Temp: 750° C.<br>P: 446 kPa | MeCl: 5 sccm<br>Temp: 300° C.<br>P: 111 kPa | 20<br>41<br>77<br>110 | 10.6<br>3.6<br>0<br>0 | 0.06<br>0.02<br>0<br>0 |
| 2 | H$_2$: 100 sccm<br>MeSiCl$_3$: 4.7 sccm<br>Temp: 750° C.<br>P: 446 kPa | MeCl: 5 sccm<br>Temp: 300° C.<br>P: 231 kPa | 22<br>54<br>80<br>101<br>121 | 26.6<br>5.6<br>2.2<br>0.9<br>0 | 0.2<br>0.08<br>0.03<br>0.01<br>0 |

Example 6

A metal catalyst comprising 4.9% Cu, 2.6% Rh, and 2.5% Re on activated carbon was prepared and treated as described in example 2. One cycle, as described in example 4, of the reaction was performed; the stainless steel bubbler was at 23° C. to give a mole ratio of H$_2$ to MeSiCl$_3$ of 6:1 in forming the silicon-containing metal intermediate. The silicon-containing metal intermediate was reacted with MeCl as in example 2 at 300° C. All of the parameters and results are listed in Table 6.

TABLE 6

| Cycle # | Step 1 | Step 2 | Time (min) | Selectivity (mol % Si products) $Me_2SiCl_2$ | Wt. % in effluent $Me_2SiCl_2$ |
|---|---|---|---|---|---|
| 1 | $H_2$: 100 sccm $MeSiCl_3$: 17.0 sccm Temp: 850° C. P: 148 kPa | MeCl: 5 sccm Temp: 300° C. P: 118 kPa | 13 35 55 89 | 70.7 31.4 10.4 0 | 0.6 0.2 0.1 0 |

Example 7

A metal catalyst comprising 6.9% Re and 1.2% Pd on activated carbon was prepared and treated as described in example 2. One cycle, as described in example 4, of the reaction was performed; the stainless steel bubbler was at 23° C. to give a mole ratio of $H_2$ to $MeSiCl_3$ of 6:1 in forming the silicon-containing metal intermediate. The silicon-containing metal intermediate was then reacted with MeCl as in example 2 at 300° C. All of the parameters and results are listed in Table 7.

TABLE 7

| Cycle # | Step 1 | Step 2 | Time (min) | Selectivity (mol % Si products) $Me_2SiCl_2$ | Wt. % $Me_2SiCl_2$ in effluent |
|---|---|---|---|---|---|
| 1 | $H_2$: 100 sccm $MeSiCl_3$: 8.1 sccm Temp: 750° C. P: 126 kPa | MeCl: 5 sccm Temp: 300° C. P: 106 kPa | 3 23 43 62 84 103 136 | 0 10.2 0 0 0 0 0 | 0 0.02 0 0 0 0 0 |

That which is claimed is:

1. A method of preparing a diorganodihalosilane, the method comprising the following separate and consecutive steps:
   (a) treating a metal catalyst comprising a metal selected from the group consisting of i) gold, ii) gold and copper, iii) gold, copper and magnesium, iv) copper, rhodium and gold, v) copper, rhodium, and rhenium, vi) rhenium and palladium, vii) copper, and viii) copper and magnesium with a mixture comprising hydrogen gas and an organotrihalosilane at a temperature from 500 to 1400° C. to form a silicon-containing metal intermediate; and
   (b) reacting the silicon-containing metal intermediate with an organohalide according to the formula RX, wherein R is $C_1$-$C_{10}$ hydrocarbyl and X is halo, at a temperature from 100 to 600° C. to form a diorganodihalosilane and a depleted silicon-containing metal intermediate.

2. The method according to claim 1, further comprising (c) contacting the depleted silicon-containing metal intermediate formed in step (b) with the hydrogen gas and the organotrihalosilane at a temperature of from 500 to 1400° C. to reform the silicon-containing metal intermediate comprising at least 0.1% (w/w) silicon; and (d) contacting the reformed silicon-containing metal intermediate with the organohalide at a temperature of from 100 to 600° C. to form a diorganodihalosilane.

3. The method according to claim 2, further comprising repeating steps (c) and (d) at least 1 time.

4. The method according to claim 2, further comprising purging prior to the contacting of the reformed silicon-containing metal intermediate with the organohalide in step (d).

5. The method according to claim 4, wherein the purging is conducted with argon or organotrihalosilane.

6. The method according to any claim 1, further comprising purging prior to contacting the silicon-containing metal intermediate with the organohalide in step (b).

7. The method according to claim 6, wherein the purging is conducted with argon or organotrihalosilane.

8. The method according to claim 1, wherein the metal catalyst further comprises a support.

9. The method according to claim 8, wherein the metal catalyst comprises from 0.1 to 35% (w/w) of the metal and the metal comprises copper, gold and magnesium.

10. The method according to claim 8, wherein the support is activated carbon.

11. The method according to claim 1, wherein the silicon-containing metal intermediate comprises from 1 to 5% (w/w) of silicon.

12. The method according to claim 1, wherein mole ratio of hydrogen to silicon tetrahalide in step (a) is from 20:1 to 5:1.

13. The method according to claim 1, wherein the organohalide is methyl chloride, and the organotrihalosilane is $CH_3SiCl_3$.

14. The method according to claim 1, further comprising recovering the diorganodihalosilane.

15. The method according to claim 1, wherein the residence time of the hydrogen and organotrihalosilane is from 1 to 10 s in step (a) and the residence time of the organohalide is from 1 to 10 s in step (b).

16. The method according to claim 1, wherein step (b) is at a pressure from 7 to 1000 kPag.

17. The method according to claim 1, wherein step (a) is at a pressure from 7 to 1000 kPag.

18. The method according to claim 1, wherein the diorganodihalosilane is dimethyldichlorosilane.

19. The method according to claim 1, wherein the method further comprises the step of hydrolyzing the diorganodihalosilane to form a polyorganosiloxane.

* * * * *